US008879275B2

(12) United States Patent
Boday et al.

(10) Patent No.: US 8,879,275 B2
(45) Date of Patent: *Nov. 4, 2014

(54) ANTI-CORROSION CONFORMAL COATING COMPRISING MODIFIED POROUS SILICA FILLERS FOR METAL CONDUCTORS ELECTRICALLY CONNECTING AN ELECTRONIC COMPONENT

(75) Inventors: Dylan J. Boday, Tucson, AZ (US); Joseph Kuczynski, Rochester, MN (US); Jason T. Wertz, Wappingers Falls, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 255 days.

This patent is subject to a terminal disclaimer.

(21) Appl. No.: 13/401,028

(22) Filed: Feb. 21, 2012

(65) Prior Publication Data

US 2013/0213707 A1  Aug. 22, 2013

(51) Int. Cl.
| | |
|---|---|
| *H05K 7/00* | (2006.01) |
| *B32B 33/00* | (2006.01) |
| *B32B 3/02* | (2006.01) |
| *D03D 27/00* | (2006.01) |
| *D04H 11/00* | (2006.01) |
| *D05C 17/00* | (2006.01) |

(52) U.S. Cl.
USPC .......................................... 361/760; 428/96.4

(58) Field of Classification Search
CPC ....................................................... B05D 5/12
See application file for complete search history.

(56) References Cited

U.S. PATENT DOCUMENTS

| | | | |
|---|---|---|---|
| 3,770,513 A | 11/1973 | Wystrach | |
| 4,668,719 A | 5/1987 | Kato et al. | |
| 4,985,477 A | 1/1991 | Collins et al. | |
| 5,969,023 A | 10/1999 | Enami et al. | |
| 6,384,125 B1 | 5/2002 | Bergstrom et al. | |
| 6,524,895 B2 * | 2/2003 | Yamazaki et al. | 438/149 |
| 6,802,753 B1 * | 10/2004 | Ando et al. | 445/6 |
| 6,808,680 B2 | 10/2004 | Kalina | |
| 6,902,656 B2 * | 6/2005 | Ouellet et al. | 204/192.16 |
| 6,972,249 B2 * | 12/2005 | Akram et al. | 438/613 |

(Continued)

FOREIGN PATENT DOCUMENTS

| | | |
|---|---|---|
| JP | 60071627 | 5/1985 |
| JP | 63006018 | 1/1988 |

(Continued)

OTHER PUBLICATIONS http://www.norpro.saint-gobain.com/lsa-catalyst-carriers.aspx, *LSA Catalyst Carriers*.

(Continued)

*Primary Examiner* — Hoa C Nguyen
*Assistant Examiner* — Xanthia C Cunningham
(74) *Attorney, Agent, or Firm* — Robert R. Williams

(57) ABSTRACT

A conformal coating comprising modified porous silica particles is disclosed. A porous silica particle, such as MCM-14 or SBA-15 is modified with a sulfur gettering functionality, such as a phosphine compound, covalently bonded to silicon atoms in the porous silica particle. The conformal coating comprising the modified porous silica particles may be applied to metallic wiring areas of a circuit component, with the sulfur gettering functionality preventing sulfur from atmospheric gasses from penetrating the conformal coating to the metallic wiring.

17 Claims, 8 Drawing Sheets

(56) References Cited

U.S. PATENT DOCUMENTS

| | | | |
|---|---|---|---|
| 7,126,276 B2* | 10/2006 | Hasegawa | 313/553 |
| 7,553,901 B2 | 6/2009 | Horikoshi et al. | |
| 7,723,407 B2 | 5/2010 | Sugioka et al. | |
| 8,323,980 B2 | 12/2012 | Boday et al. | |
| 8,486,533 B2 | 7/2013 | Boday et al. | |
| 2003/0030155 A1 | 2/2003 | Toyoda et al. | |
| 2003/0141802 A1* | 7/2003 | Liebeskind et al. | 313/495 |
| 2003/0181024 A1* | 9/2003 | Takeuchi et al. | 438/477 |
| 2005/0245649 A1 | 11/2005 | Parent et al. | |
| 2007/0099005 A1 | 5/2007 | Leung et al. | |
| 2007/0257091 A1 | 11/2007 | Kuczynski et al. | |
| 2008/0226902 A1* | 9/2008 | Giannantonio et al. | 428/336 |
| 2008/0255293 A1 | 10/2008 | Sasaki et al. | |
| 2009/0008715 A1* | 1/2009 | Yamazaki | 257/347 |
| 2009/0102055 A1* | 4/2009 | Aoki et al. | 257/773 |
| 2009/0114093 A1* | 5/2009 | Li et al. | 95/135 |
| 2009/0141472 A1 | 6/2009 | Choi et al. | |
| 2009/0274936 A1* | 11/2009 | Goldstein et al. | 429/13 |
| 2010/0112454 A1* | 5/2010 | Visco et al. | 429/246 |
| 2010/0157165 A1* | 6/2010 | Hiroki et al. | 348/730 |
| 2010/0240173 A1* | 9/2010 | Fujii | 438/104 |
| 2010/0273310 A1* | 10/2010 | Hanaoka et al. | 438/458 |
| 2010/0314544 A1* | 12/2010 | Ouvrier-Buffet | 250/338.4 |
| 2011/0184087 A1 | 7/2011 | Campomizzi et al. | |
| 2011/0189381 A1* | 8/2011 | Boday et al. | 427/58 |
| 2011/0236985 A1 | 9/2011 | Boday et al. | |
| 2013/0213707 A1 | 8/2013 | Boday et al. | |

FOREIGN PATENT DOCUMENTS

| | | |
|---|---|---|
| JP | 01113454 A | 5/1989 |
| JP | 06100313 A | 4/1994 |
| JP | 2000063392 | 2/2000 |
| JP | 2010017644 A | 1/2010 |
| WO | 02064855 A1 | 8/2002 |

OTHER PUBLICATIONS http://www.cheric.org/research/tech/periodicals/view.phy?seq=692291, Cheric, "Selective removal of sulfur compounds in city-gas by adsorbents", Korean Journal of Chemical Engineering, vol. 24, No. 6, 1124-1127, 2007.

http:/www.chm.bris.ac.uk/motm/mcm41/mcm41.html, "Molecule of the Month", MCM-41, Vladimir Gusev.

http://en.wikipedia.org/wiki/Triphenylphosphine, "Triphenylphosphine" From Wikipedia.

U.S. Appl. No. 13/327,971, entitled "High Surface Area Filler for Use in Conformal Coating Compositions", filed Dec. 16, 2011.

* cited by examiner

ANTI-CORROSION CONFORMAL COATING COMPRISING MODIFIED POROUS SILICA FILLERS FOR METAL CONDUCTORS ELECTRICALLY CONNECTING AN ELECTRONIC COMPONENT

BACKGROUND OF THE INVENTION

1. Field of Invention

The present invention relates in general to the field of electronic packaging. More particularly, the present invention relates to a polymer conformal coating comprising modified porous silica fillers which contains a phosphine compound that provides corrosion protection for metal conductors electrically connecting one or more electronic components (e.g., the discrete gate resistors in a resistor network array) mounted on a substrate such as a printed circuit board.

2. Background Art

Electronic components, such as microprocessors and integrated circuits, are generally packaged using electronic packages (i.e., modules) that include a module substrate to which one or more electronic component(s) is/are electronically connected. A single-chip module (SCM) contains a single electronic component such as a central processor unit (CPU), memory, application-specific integrated circuit (ASIC) or other integrated circuit. A multi-chip module (MCM), on the other hand, contains two or more such electronic components.

Generally, each of these electronic components takes the form of a flip-chip, which is a semiconductor chip or die having an array of spaced-apart terminals or pads on its base to provide base-down mounting of the flip-chip to the module substrate. The module substrate is typically a ceramic carrier or other conductor-carrying substrate.

Controlled collapse chip connection (C4) solder joints (also referred to as "solder bumps") are typically used to electrically connect the terminals or pads on the base of the flip-chip with corresponding terminals or pads on the module substrate. C4 solder joints are disposed on the base of the flip-chip in an array of minute solder balls (e.g., on the order of 100 µm diameter and 200 µm pitch). The solder balls, which are typically lead (Pb)-containing solder but may be lead-free solder (e.g., Sn—Ag—Cu solder), are reflowed to join (i.e., electrically and mechanically) the terminals or pads on the base of the flip-chip with corresponding terminals or pads on the module substrate.

Typically, a non-conductive polymer underfill is disposed in the space between the base of the flip-chip and the module substrate and encapsulates the C4 solder joints. The C4 solder joints are embedded in this polymeric underfill and are thus protected from corrosion caused by moisture and carbon dioxide in the air, as well as octanoic acid outgassed from components within the module. However, the use of the polymeric chip underfill may not adequately protect the C4 solder joints from corrosion caused by sulfur components (e.g., elemental sulfur, hydrogen sulfide, and/or sulfur oxides) in the air, especially if the C4 solder joints contain silver as a significant constituent.

It is also known to cover the C4 solder joints with a conformal coating, such as a cast polymer barrier layer, to protect the C4 solder joints from corrosion caused by moisture and carbon dioxide in the air, as well as octanoic acid outgassed from components within the module. For example, U.S. Patent Application Publication No. 2007/0257091 A1, entitled "Chip Module having Solder Balls Coated with a Thin Cast Polymer Barrier Layer for Corrosion Protection and Reworkability, and Method for Making Same" and published on Nov. 8, 2007, to Kuczynski, discloses a thin cast polymer barrier layer covering solder joints that not only protects the solder joints from corrosion caused by moisture and carbon dioxide in the air (as well as octanoic acid outgassed from components within the module), but also provides reworkability. The cast polymer barrier layer is selected from suitable polymers including polystyrene; poly(oxymethyleneoxyethylene); poly(oxybutylethylene); poly(vinylidene chloride); poly(perfluoro-4-chloro-1,6-heptadiene); poly(methacrylic acid), ethyl ester; poly(methacrylic acid), n-propyl ester; poly(methacrylic acid), i-propyl ester; poly (methacrylic acid), n-butyl ester; poly(methacrylic acid), i-butyl ester; poly(methacrylic acid), sec-butyl ester; poly (methacrylic acid), n-amyl ester; poly(methacrylic acid), i-amyl ester; poly(methacrylic acid), 1,2-dimethylpropyl ester; poly(methacrylic acid), neopentyl ester; poly(methacrylic acid), 3,3-dimethylbutyl ester; poly(methacrylic acid), 1,3-dimethylbutyl ester; poly(perfluoropropylene); poly(vinyl alcohol); poly(vinyl butyrate); poly(methyl isopropenyl ketone); and combinations thereof. Unfortunately, like the polymeric chip underfill, the use of such a conformal coating may not adequately protect the C4 solder joints from corrosion caused by sulfur components (e.g., elemental sulfur, hydrogen sulfide, and/or sulfur oxides) in the air, especially if the C4 solder joints contain silver as a significant constituent.

It is also known to use silicon nitride ($Si_3N_4$) to seal a flip-chip. For example, U.S. Pat. No. 6,972,249 B2, entitled "Use of Nitrides for Flip-Chip Encapulation" and issued Dec. 6, 2005 to Akram et al., discloses a semiconductor flip-chip that is sealed with a silicon nitride layer on an active surface of the flip-chip. The silicon nitride layer covers the chip active surface, including the bond pads and conductive connectors such as solder balls formed over the bond pads. Unfortunately, while the silicon nitride layer may provide some degree of protection for the bond pads and conductive connectors from corrosion caused by sulfur components (e.g., elemental sulfur, hydrogen sulfide, and/or sulfur oxides) in the air, the silicon nitride layer is difficult to process and work with.

The problem of corrosion caused by sulfur components (e.g., elemental sulfur, hydrogen sulfide, and/or sulfur oxides) in the air is especially severe when one or more of the metal conductors that electrically connect an electronic component is/are a silver-containing metal. For example, each of the gate resistors of a resistor network array typically utilizes a silver layer at each of the gate resistor's terminations. Gate resistors are also referred to as "chip resistors" or "silver chip resistors". Typically, gate resistors are coated with a glass over coat for corrosion protection. Also for corrosion protection, it is known to encapsulate gate resistors in a resistor network array by applying a coating of a conventional room temperature-vulcanizable (RTV) silicone rubber composition over the entire printed circuit board on which the resistor network array is mounted. However, the glass over coat and conventional RTV silicone rubber compositions fail to prevent or retard sulfur components in the air from reaching the silver layer in gate resistors. Hence, any sulfur components in the air will react with the silver layer in the gate resistor to form silver sulfide. This silver sulfide formation often causes the gate resistor to fail, i.e., the formation of silver sulfide, which is electrically non-conductive, produces an electrical open at one or more of the gate resistor's terminations.

FIG. 1 illustrates, in an exploded view, an example of a conventional gate resistor 100 of a resistor network array. A resistor element 102 is mounted to a substrate 104, such as a ceramic substrate. The gate resistor 100 includes two termination structures 110, each typically comprising an inner Ag (silver) layer 112, a protective Ni (nickel) barrier layer 114, and an outer solder termination layer 116. Typically, for corrosion protection, the gate resistor 100 is coated with a glass over coat 120. Additionally, for corrosion protection, a coating (not shown) of a conventional RTV silicone rubber composition may encapsulate the gate resistor 100. As noted above, it is known to encapsulate gate resistors in a resistor network array mounted on a printed circuit board by applying a coating of a conventional RTV silicone rubber composition over the entire board. However, as noted above, the glass over coat 120 and conventional RTV silicone rubber compositions fail to prevent or retard sulfur components in the air from reaching the inner silver layer 112. Hence, any sulfur components in the air will react with the inner silver layer 112 to form silver sulfide 202 (shown in FIG. 2). FIG. 2 illustrates, in a sectional view, the conventional gate resistor 100 shown in FIG. 1, but which has failed due to exposure to sulfur-bearing gases. The silver sulfide formation 202 (often referred to as silver sulfide "whiskers") produces an electrical open at one or more of the gate resistor's terminations 110 because silver sulfide is an electrical non-conductor and, thereby, results in failure of the gate resistor 100.

The use of silver as an electrical conductor for electrically connecting electronic components is increasing because silver has the highest electrical conductivity of all metals, even higher than copper. In addition, the concentration of sulfur components in the air is unfortunately increasing as well. Hence, the problem of corrosion caused by sulfur components in the air is expected to grow with the increased use of silver as an electrical conductor for electrically connecting electronic components and the increased concentration of sulfur components in the air.

U.S. Pat. No. 7,553,901 B2, entitled "RTV Silicone Rubber Composition for Electric and Electronic Part Protection, Circuit Boards, Silver Electrodes, and Silver Chip Resistors" and issued on Jun. 30, 2009 to Horikoshi et al., discloses RTV silicone rubber compositions comprising an organopolysiloxane, an organosilicon compound or partial hydrolytic condensate thereof, and a non-aromatic amino-bearing compound. The compositions are purported to prevent or retard electronic parts encapsulated or sealed therewith from corrosion with sulfur-containing gas. However, the amino-bearing compound in the compositions binds not only with sulfur components in the air but, disadvantageously, binds with carbon dioxide in the air. Hence, the amino-bearing compound in the compositions is quickly consumed by carbon dioxide in the air and is not available to bind with sulfur components in the air. The amino-bearing compound in the compositions also disadvantageously binds to tin catalyst, which is typically required in the formation of RTV silicone rubber compositions. In addition, the amino-bearing compound, though non-aromatic, is nonetheless not completely non-volatile because it is not bonded directly to the polysiloxane backbone.

Therefore, a need exists for an enhanced composition, method and apparatus for protecting metal conductors for electrically connecting electronic components from corrosion caused by sulfur components (e.g., elemental sulfur, hydrogen sulfide, and/or sulfur oxides) in the air.

SUMMARY OF THE INVENTION

According to the preferred embodiments of the present invention, an apparatus includes an electronic component mounted on a substrate and metal conductors electronically connecting the electronic component. A conformal coating comprising modified porous silica fillers overlies or surrounds the metal conductors. The conformal coating comprises a polymer into which a porous silica filler is mixed. The porous silica filler is modified with a gettering functionality such as a phosphine compound having covalent bonds with atoms in the porous silica filler. Accordingly, the conformal coating is able to protect the metal conductors from corrosion caused by sulfur components (e.g., elemental sulfur, hydrogen sulfide, and/or sulfur oxides) in the air. That is, the phosphine compound in the porous silica filler in the polymer reacts with any corrosion inducing sulfur component in the air and prevents the sulfur component from reacting with the underlying metal conductors. This can significantly extend the life of the electronic component. Preferably, the phosphine compound in the porous filter of the polymer does not react with other components in the air (e.g., carbon dioxide) which would otherwise deplete its availability for the target reaction.

BRIEF DESCRIPTION OF THE DRAWINGS

The preferred exemplary embodiments of the present invention will hereinafter be described in conjunction with the appended drawings, where like designations denote like elements.

DETAILED DESCRIPTION OF THE PREFERRED EMBODIMENTS

1. Overview

In accordance with the preferred embodiments of the present invention, an apparatus includes an electronic component mounted on a substrate and metal conductors electrically connecting the electronic component. A conformal coating overlies the metal conductors and comprises a polymer into which a phosphine compound is impregnated and/or covalently bonded. Accordingly, the conformal coating is able to protect the metal conductors from corrosion caused by sulfur components (e.g., elemental sulfur, hydrogen sulfide, and/or sulfur oxides) in the air. That is, the phosphine compound in the polymer reacts with any corrosion inducing sulfur component in the air and prevents the sulfur component from reacting with the underlying metal conductors. This can significantly extend the life of the electronic component. Preferably, the phosphine compound in the polymer does not react with other components in the air (e.g., carbon dioxide) which would otherwise deplete its availability for the target reaction. The phosphine compound may be rendered completely non-volatile by covalently bonding it directly into the polymer backbone.

2. Detailed Description

The present invention is described herein in the context of protecting metal conductors of an exemplary gate resistor in a resistor network array from corrosion caused by sulfur components in the air. One skilled in the art will appreciate, however, that the present invention can also apply to protecting metal conductors of gate resistors and resistor network arrays having configurations differing from the gate resistor and resistor network array shown in FIGS. 3-5 and to protecting metal conductors of other electronic components, and, more generally, to protecting a metal surface of any product. For example, the present invention can be used to protect controlled collapse chip connection (C4) solder joints that electrically connect terminals or pads on the base of a flip-chip with corresponding terminals or pads on a module substrate.

Figure 3:
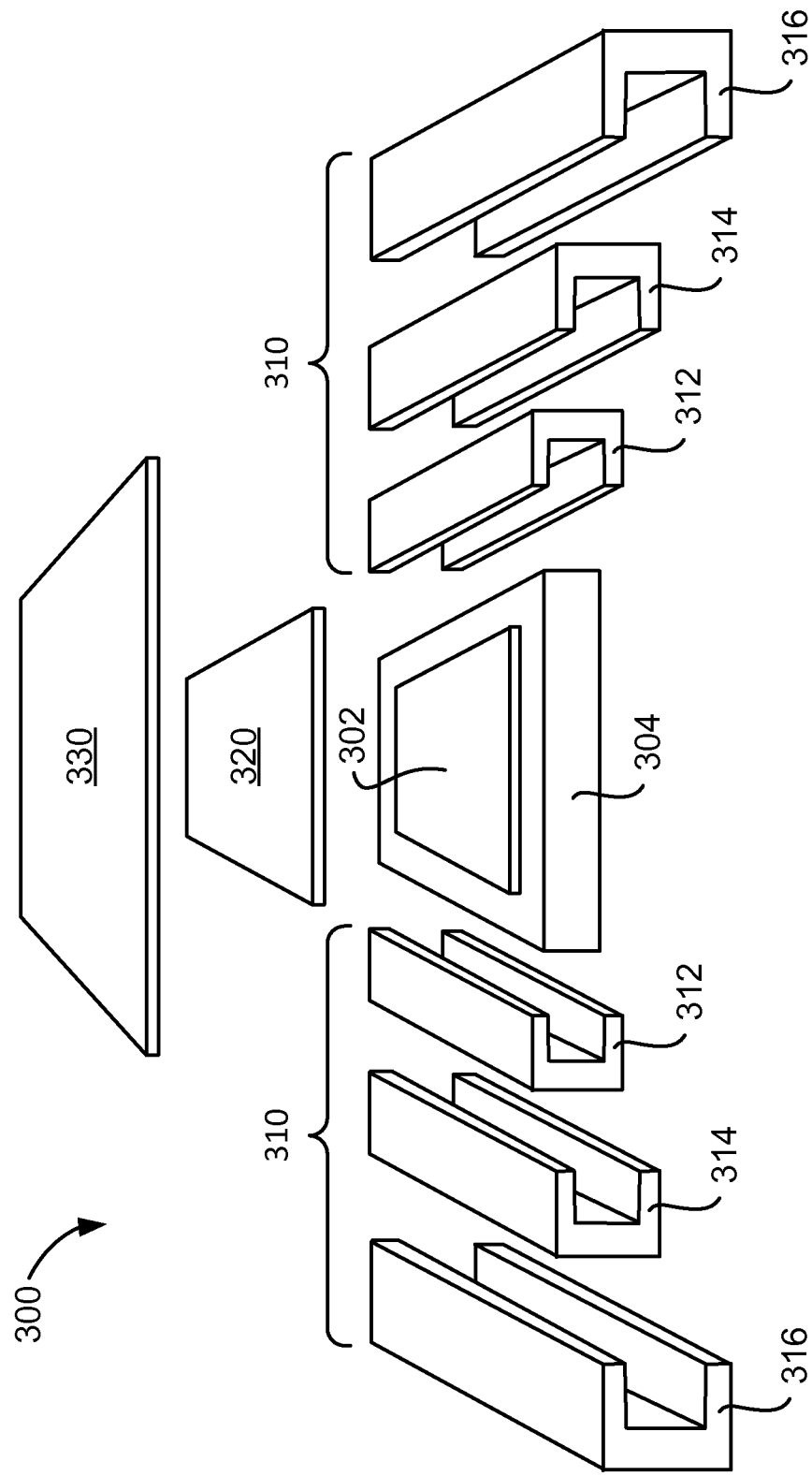
FIG. 3 is an exploded view of a gate resistor of a resistor network array that utilizes a phosphine-containing polymer conformal coating to protect metal conductors according to the preferred embodiments of the present invention.
Figure 4:
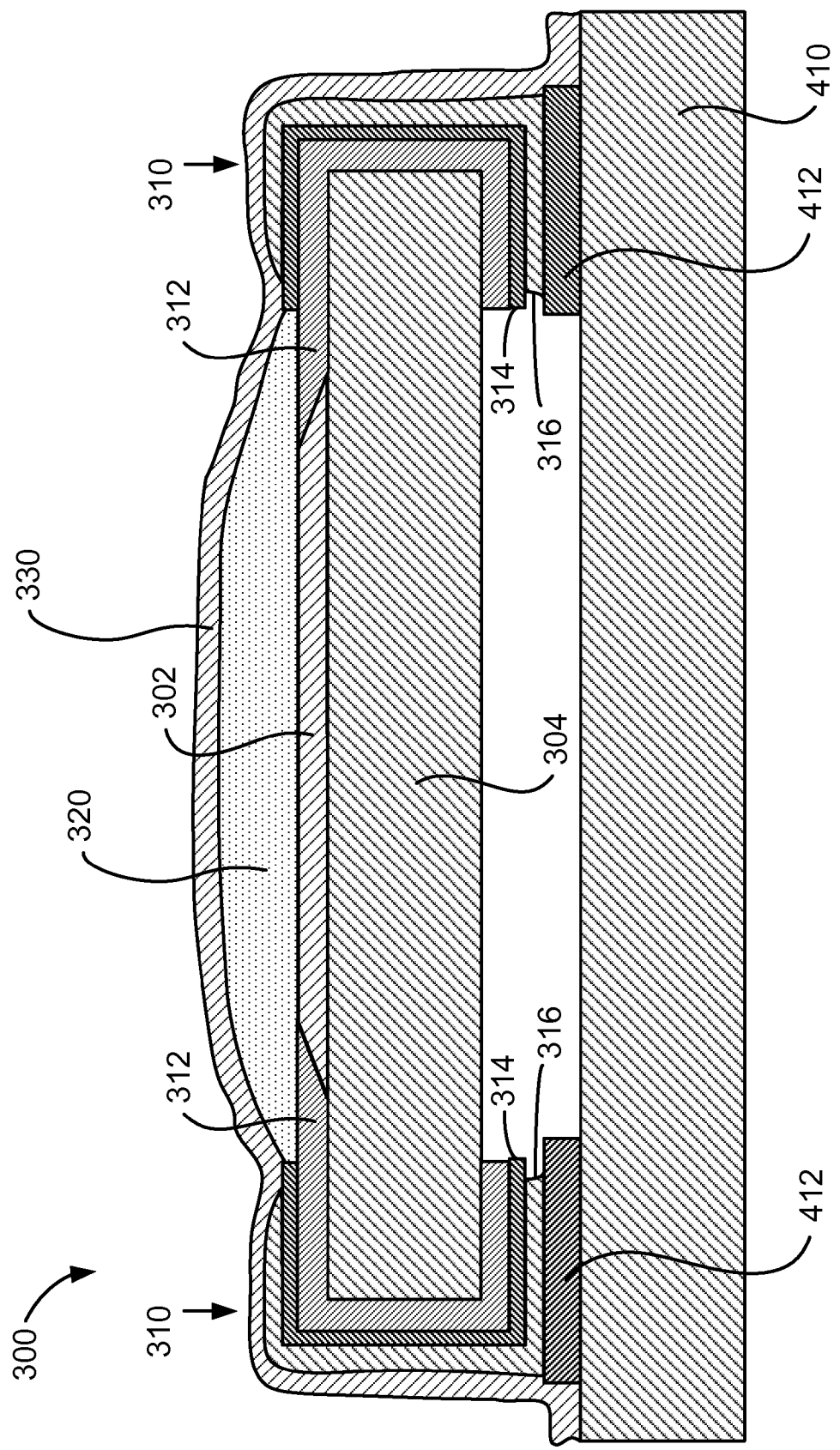
FIG. 4 is a sectional view of the gate resistor shown in FIG. 3, but which is shown mounted on a printed circuit board.
Figure 5:
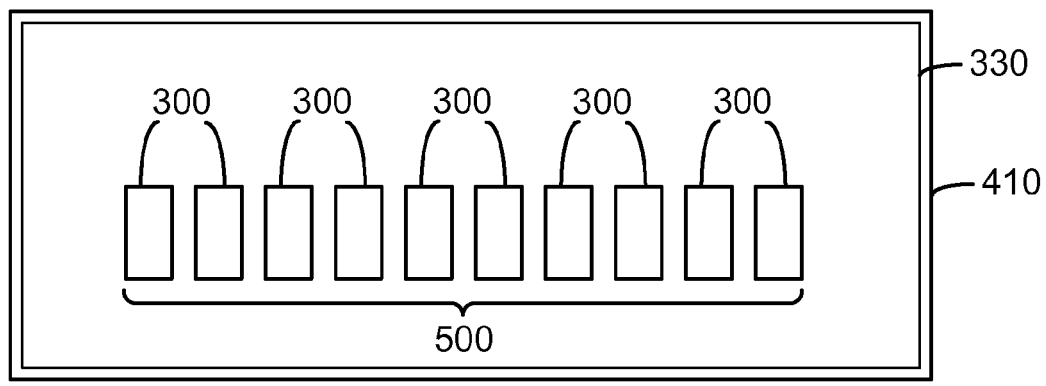
FIG. 5 is a top view of a resistor network array mounted on a printed circuit board that utilizes a phosphine-containing polymer conformal coating to protect metal conductors according to the preferred embodiments of the present invention.

Referring now to FIG. 3, there is depicted, in an exploded view, a gate resistor 300 of a resistor network array (shown in FIG. 5) that utilizes a phosphine-containing polymer conformal coating 330, which according to the preferred embodiments of the present invention, provides corrosion protection for metal conductors. FIG. 4 is a sectional view of the gate resistor 300 shown in FIG. 3, but which is shown mounted on a printed circuit board 410. FIG. 5 is a top view of a resistor network array 500 that utilizes the phosphine-containing polymer conformal coating 330 shown in FIGS. 3 and 4.

As shown in FIGS. 3 and 4, a resistor element 302 is mounted to a substrate 304, such as a ceramic substrate. The gate resistor 300 includes two termination structures 310, each typically comprising an inner Ag (silver) layer 312, a protective Ni (nickel) barrier layer 314, and an outer solder termination layer 316. Each of the termination structures 310 of the gate resistor 300 is also referred to herein as a "metal conductor".

Typically, for corrosion protection, each gate resistor in a resistor network array is coated with a conventional protective coating, such as a glass over coat 320.

The gate resistors in a resistor network array are typically soldered to a printed circuit board by SMT (surface mounting technology) processes. As best seen in FIG. 4, the termination structures 310 of each gate resistor 300 in the resistor network array 500 (shown in FIG. 5) are soldered to corresponding terminals or pads 412 on the printed circuit board 410. For example, the outer solder termination layer 316 of the termination structures 310 of each gate resistor 300 may be reflowed to join (i.e., electrically and mechanically) the termination structures 310 on the base of the gate resistor 300 with the corresponding terminals or pads 412 on the printed circuit board 410.

As best seen in FIG. 5, in accordance with the preferred embodiments of the present invention, the phosphine-containing polymer conformal coating 330 covers essentially the entire printed circuit board 410, encapsulating each of the gate resistors 300 of the resistor network array 500 (as well as any other discrete electronic component(s) mounted on the board 410). Hence, the phosphine-containing polymer conformal coating 330 overlies the metal conductors 310 of the gate resistor 300 to provide corrosion protection, i.e., the phosphine-containing polymer conformal coating 330 protects the metal conductors 310 of the gate resistor 300 from corrosion caused by sulfur components (e.g., elemental sulfur, hydrogen sulfide, and/or sulfur oxides) in the air.

Alternatively, the phosphine-containing polymer conformal coating 330 may cover only one or more specific areas of the printed circuit board 410 that is/are susceptible to corrosion caused by sulfur components in the air (e.g., the area of the printed circuit board 410 encompassing the resistor network array 500).

The phosphine-containing polymer conformal coating 330 has sulfur gettering functionality which can significantly extend the product life when the gate resistor 300 (or other electronic component) is to be used in a corrosive gas environment. This benefit of the present invention is achieved without affecting the operation of the gate resistor 300 (or other electronic component).

Advantageously, existing deposition processes may be used for applying the conformal coating 330 to the printed circuit board 410, and thereby encapsulate the resistor network array 500 and other discrete electronic component(s) mounted on the printed circuit board 410. The present invention may be implemented in any currently used conformal coating process utilized in the preparation of electronic components. Numerous processes conformally coat components with polymers. A phosphine compound may be impregnated into and/or covalently bonded to these polymers within the scope of the present invention. In effect, a phosphine-containing polymer conformal coating in accordance with the present invention replaces a conventional polymer conformal coating. Typically, there would be neither a significant change in the processing of components nor a significant change in the cost of conformally coating the components.

Moreover, one skilled in the art will appreciate that the present invention is not limited to use in the preparation of electronic components. Indeed, the present invention may be implemented in any currently used conformal coating process utilized in the preparation of any product (e.g., painting the metal surfaces of automobiles, appliances, road signs, etc.).

The conformal coating 330 is composed of a polymer into which a phosphine compound is impregnated and/or covalently bonded. The phosphine compound may be, for example, impregnated into the conformal coating 330 by mixing the phosphine compound with the polymer. In this case, the phosphine compound is merely blended in with the polymer (as opposed to being covalently bonded to the polymer). On the other hand, covalently bound sulfur-gettering functionalities (i.e., provided by the phosphine compound) may be advantageous (e.g., for volatile sulfur-gettering species). It may be desirable, for example, to covalently bond the phosphine compound directly into the polymer backbone and, thereby, render the phosphine compound completely non-volatile.

Conformal coatings typically fall into one of several generic classes: silicones, epoxies, acrylates, or other organic materials. Hence, the polymer in the conformal coating 330 may be, for example, one or more silicone-based polymers, one or more epoxy-based polymers, one or more acrylate-based polymers, and/or one or more other organic materials; and combinations thereof. For example, the polymer may be the substituted phosphine polysiloxane of formula (1):

Polymer (1)

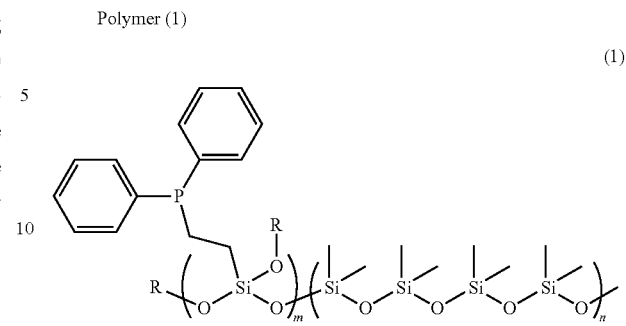

(1)

wherein each silicon atom in the substituted polysiloxane of polymer (1) is attached to a hydrogen atom, an alkyl group, or an aryl group; and wherein:
R is a hydrogen atom, an alkyl group, or an aryl group,
m is an integer of at least 1, and
n is an integer of at least 1.

An example of an epoxy-based polymer that includes a covalently-bound phosphine compound is depicted in formula (2):

(2)

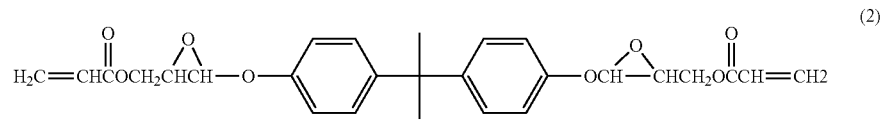

Acrylated epoxy resin

+

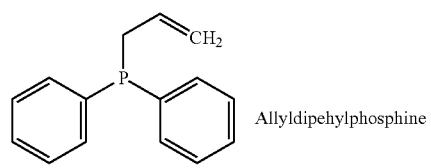

Allyldipehylphosphine

↓ AIBN

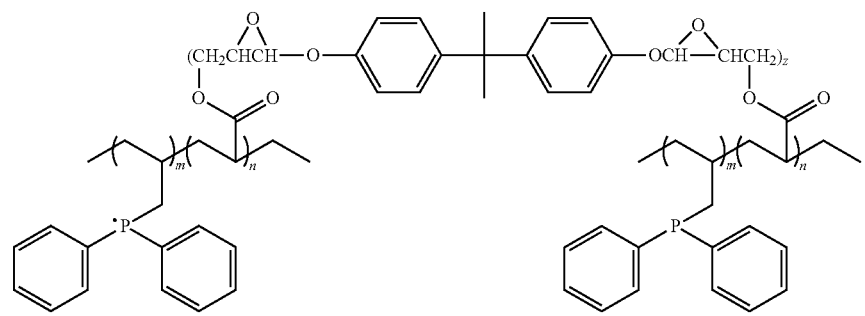

Polymer (2)

wherein z, m and n are integers of at least 1. In the foregoing example, a commercially available acrylated epoxy is reacted with allyldiphenylphosphine in the presence of AIBN (or some other suitable free radical initiator known to those skilled in the art) to form polymer (2), which is a covalently bound phosphine epoxy resin. For use as a conformal coating, polymer (2) would be reacted with a suitable epoxy crosslinking agent (e.g., photogenerated acid, a Lewis acid, an amine, phenols, etc.) to form the protective coating.

An example of an acrylate-based polymer that includes a covalently-bound phosphine compound is depicted in formula (3):

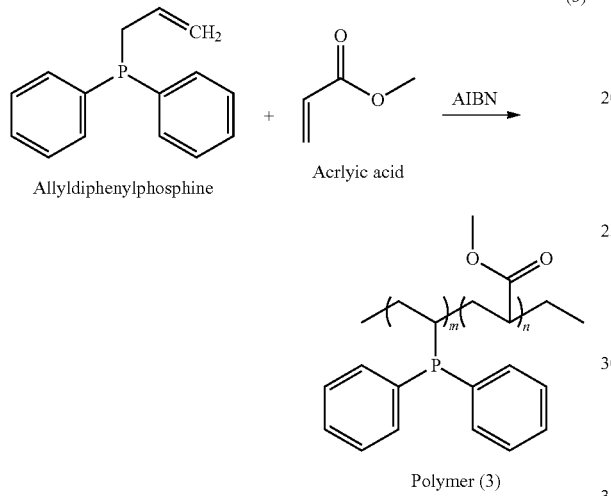

Polymer (3)

wherein m and n are integers of at least 1. In the foregoing example, allyldiphenylphosphine is reacted with acrylic acid in the presence of AIBN (or some other suitable free radical initiator known to those skilled in the art) to form polymer (3), which is a covalently bound phosphine acrylic resin.

Additional silicone-based polymers (i.e., polymer (4) and polymer (5), below) with covalently-bound phosphine functionality may be synthesized using the following scheme in formulas (4) and (5):

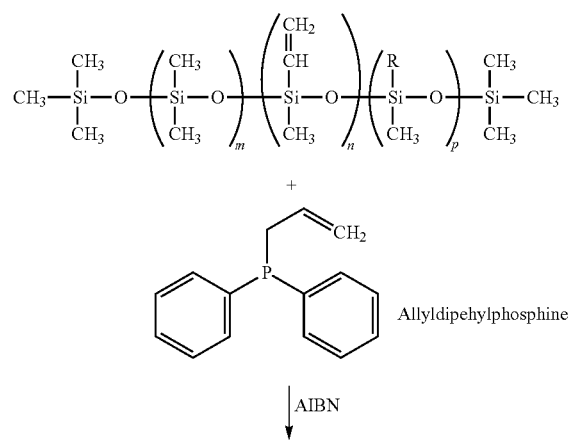

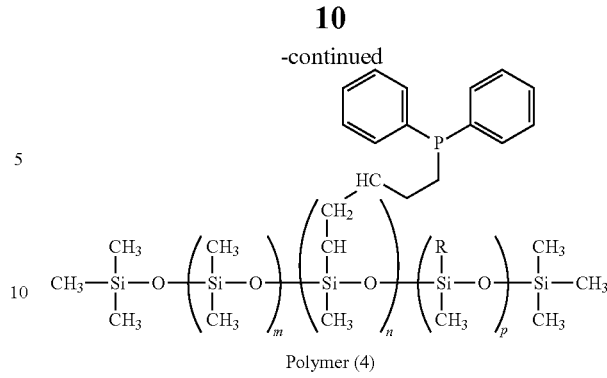

Polymer (4)

wherein m, n and p are integers of at least 1.

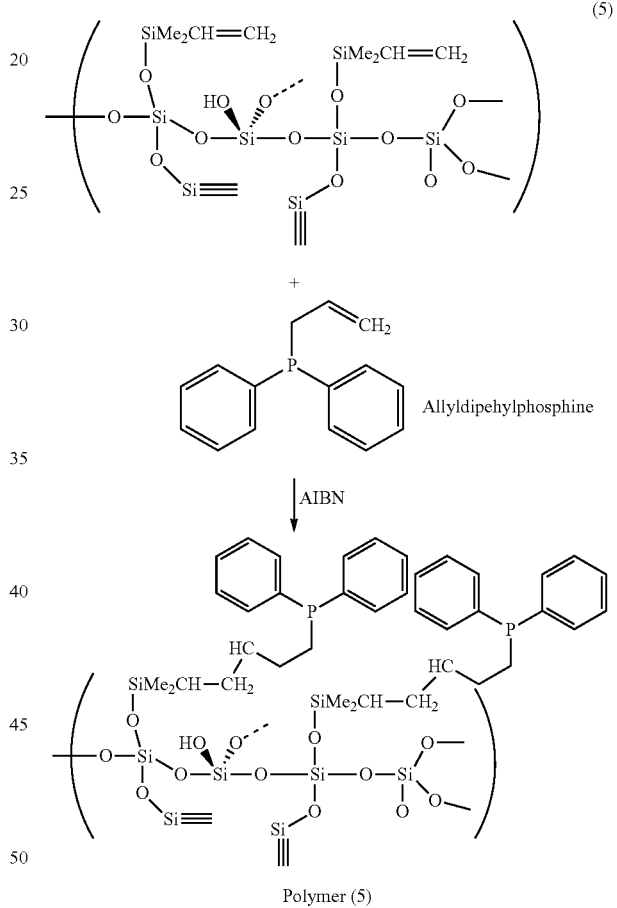

Polymer (5)

In the foregoing example, allyldiphenylphosphine is reacted with a respective precursor in the presence of AIBN (or some other suitable free radical initiator known to those skilled in the art) to form polymer (4) and polymer (5), respectively, each of which is a covalently bound phosphine polysiloxane.

The phosphine compound is a sulfur-getter that prevents the target corrosive species (i.e., sulfur components in the air) from ever reaching the metallurgy by which the electronic component is electrically connected, thus eliminating possible corrosion. The phosphine compound may be, for example, one or more alkyl phosphines and/or one or more aryl phosphines; and combinations thereof. More particularly, the phosphine compound may be one or more substituted or unsubstituted butyl phosphines and one or more substituted or unsubstituted phenyl phosphines; and combinations thereof. For example, the phosphine compound may be a substituted phenyl phosphine of formula (6):

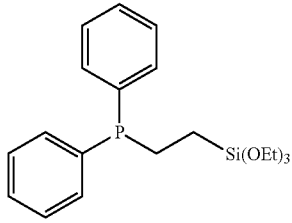

(6)

Additional exemplary phosphine compounds are depicted in the following formulas (7) and (8):

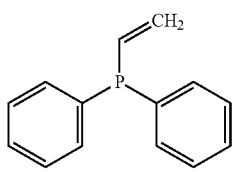

Diphenylvinylphosphine (7)

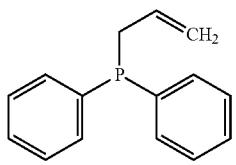

Allyldiphenylphosphine (8)

Below is a list of other examples of phosphine containing compounds which are capable of becoming covalently linked into the conformal coating using the most common conformal coatings:
(4-Hydroxyphenyl)diphenylphosphine;
2-(Diphenylphosphino)ethylamine;
3-(Diphenylphosphino)-1-propylamine;
Diallylphenylphosphine;
Diphenylphosphinostyrene;
Triallylphenylphosphine;
2-(Diphenylphosphino)ethyl-trimethoxysilane.

It will be appreciated by those skilled in the art that, in accordance with the preferred embodiments of the present invention, the intent is to covalently bind a phosphine-functional group into a polymer backbone to provide the sulfur-getting feature of the conformal coating. As such, numerous phosphine derivatives or phosphine oxide derivatives can be envisaged that will accomplish the intended task. The foregoing examples are merely representative of the synthetic scheme utilized to create the polymer of interest.

In yet another embodiment, phosphine containing compounds such as triphenylphosphine, Dicyclohexyl(2-methylphenyl)phosphine, 4-(Dimethylamino)phenyldiphenylphosphine, Tribenzylphosphine, Benzyldiphenylphosphine, Cyclohexyldiphenylphosphine, and Bis(2-methoxyphenyl)phenylphosphine can be impregnated into a conformal coating such as polysiloxanes, polyepoxide and polyacrylates. The concentration of the phosphine containing compounds which would be impregnated into the conformal coating could range from 0.01-20 wt %, preferably 0.1-10 wt % and most preferably 0.5-5 wt %. The above-listed exemplary phosphine containing compounds, conformal coatings and concentrations are set forth for the purpose of illustration, not limitation. Those skilled in the art will appreciate that other phosphine containing compounds, conformal coatings, and/or concentrations may be used within the scope of the present invention.

The gettering functionality of the phosphine compound binds and traps the target corrosive species (i.e., sulfur components in the air). Binding this corrosive species prevents the diffusion of the corrosive species to the underlying metallurgy. If just a polymer coating was used, diffusion of the corrosive species would still occur. Polymer coatings only slow, but do not trap, the corrosive species. The phosphine compound, being a sulfur-getter, works by attacking the sulfur-sulfur bond in the corrosive species, breaking it and remaining covalently bonded to it. Hence the corrosive species is trapped, which prevents the further diffusion toward the surface of the electronic component. This eliminates the possibility of the corrosive species reaching the underlying metallurgical surfaces of the electronic component, and thus prevents corrosion of those metallurgical surfaces.

Preferably, the phosphine compound in the polymer does not react with non-sulfur components in the air (e.g., carbon dioxide) which would otherwise deplete the availability of the phosphine compound for the target reaction (i.e., reaction with sulfur components in the air). This contrasts with enhanced RTV silicone rubber compositions known in the prior art that utilize an amino-bearing compound to prevent or retard electronic parts encapsulated or sealed therewith from corrosion with sulfur-containing gas, in which the amino-bearing compound binds not only with the sulfur components in the air but, disadvantageously, with carbon dioxide in the air. Hence, the amino-bearing compound in such prior art RTV silicone rubber compositions is quickly consumed by carbon dioxide in the air and is not available to bind with sulfur components in the air. The amino-bearing compound in such prior art RTV silicone rubber compositions also disadvantageously binds to tin catalyst, which is typically required in the formation of RTV silicone rubber compositions.

In accordance with the preferred embodiments of the present invention, the conformal coating 330 is a substituted phosphine polysiloxane conformal coating, a substituted phosphine polyacrylate conformal coating, or a substituted phosphine polyepoxide conformal coating. For example, the conformal coating may be polymer (1) depicted below, a substituted phosphine polysiloxane.

Polymer (1)

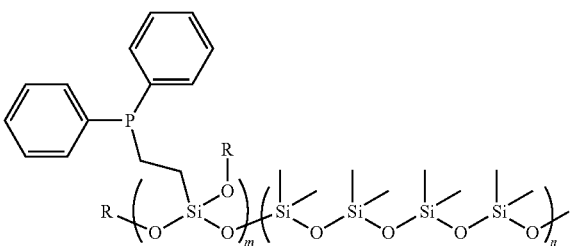

wherein each silicon atom in the polysiloxane is attached to a hydrogen atom, an alkyl group, or an aryl group; and wherein:
R is a hydrogen atom, an alkyl group, or an aryl group,
m is an integer of at least 1, and
n is an integer of at least 1.

Representative examples of epoxy-based and acrylate-based, covalently bound phosphine polymers suitable for use in the formulation of conformal coatings are depicted below (i.e., polymer (2) and polymer (3), respectively).

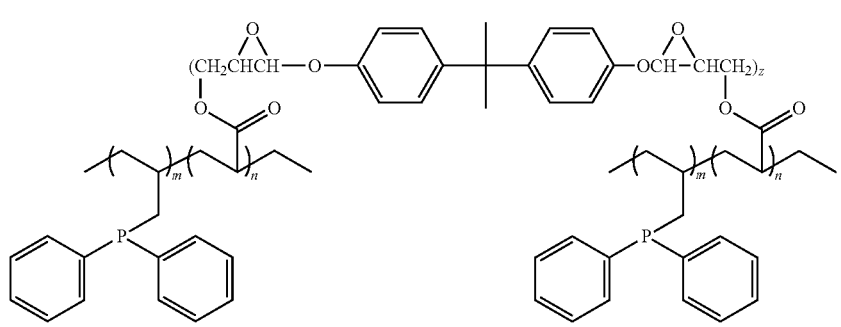

Polymer (2)

wherein z, m and n are integers of at least 1.

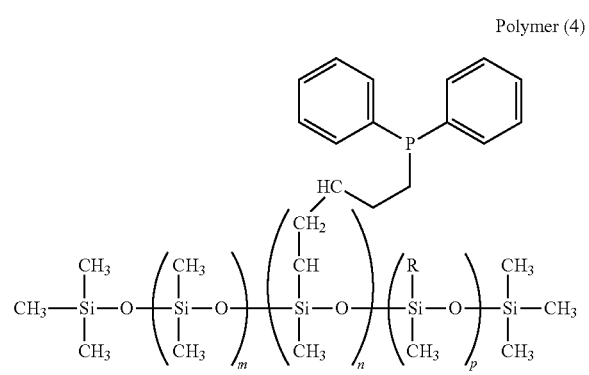

Polymer (3)

wherein m and n are integers of at least 1.

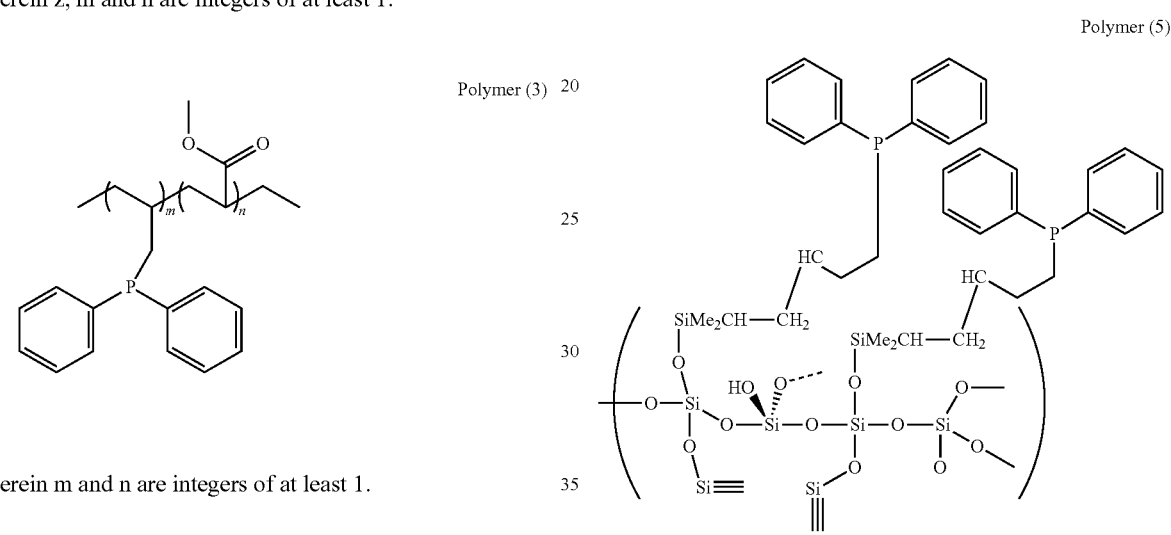

Polymer (5)

Additional polysiloxane polymers suitable for use in the formulation of conformal coatings are depicted below (i.e., polymer (4) and polymer (5)).

Polymer (4)

wherein m, n and p are integers of at least 1.

Figure 1:
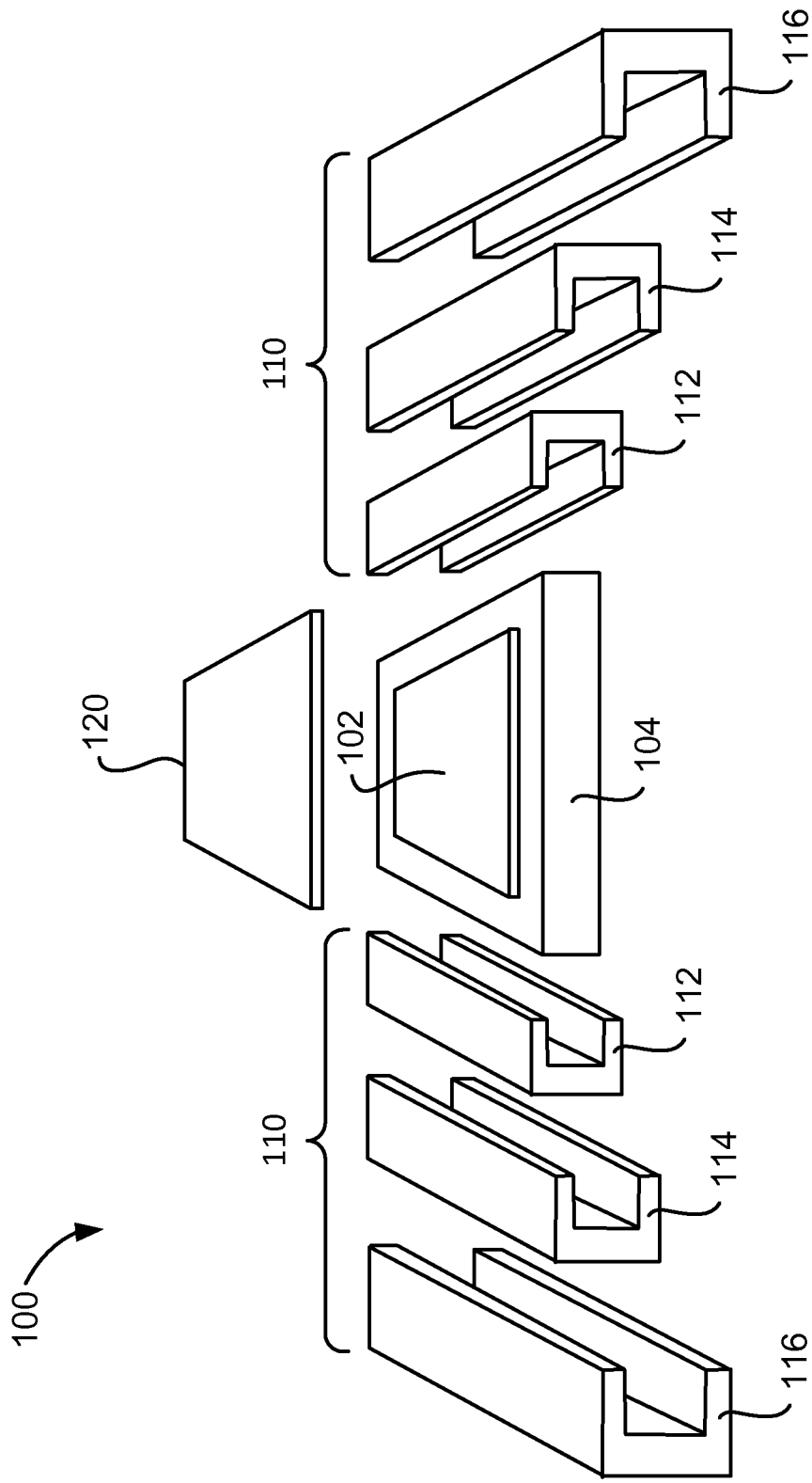
FIG. 1 is an exploded view of a conventional gate resistor of a resistor network array.
Figure 2:
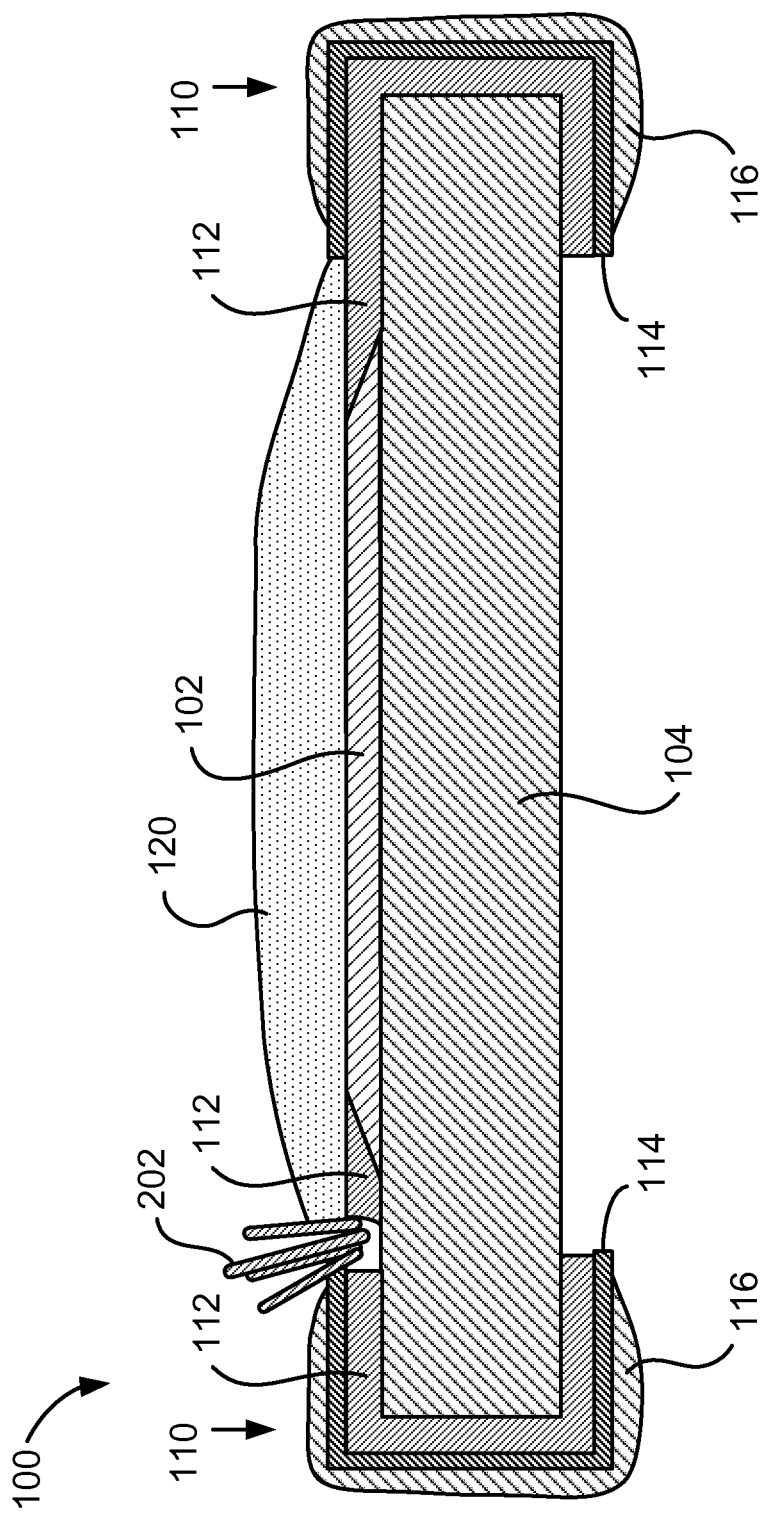
FIG. 2 is a sectional view of the conventional gate resistor shown in FIG. 1, but which has failed due to exposure to sulfur-bearing gases.

Conventional gate resistors, such as the conventional gate resistor 100 (shown in FIGS. 1 and 2), are typically coated with an overcoat of a conventional RTV silicone rubber composition that fails to prevent or retard sulfur components in the air from reaching the inner silver layer. Hence, any sulfur components in the air will react with the inner silver layer to form silver sulfide, which is electrically non-conductive. The silver sulfide formation (often referred to as silver sulfide "whiskers") produces an electrical open at one or more of the terminations of the gate resistor and, thereby, failure of the gate resistor.

In contrast, the phosphine-containing polymer conformal coating of the present invention is able to protect the metal conductors from corrosion caused by sulfur components (e.g., elemental sulfur, hydrogen sulfide, and/or sulfur oxides) in the air. The phosphine compound in the conformal coating of the present invention reacts with any corrosion inducing sulfur component in the air and prevents the sulfur component from reacting with the underlying metal conductors.

Figure 6:
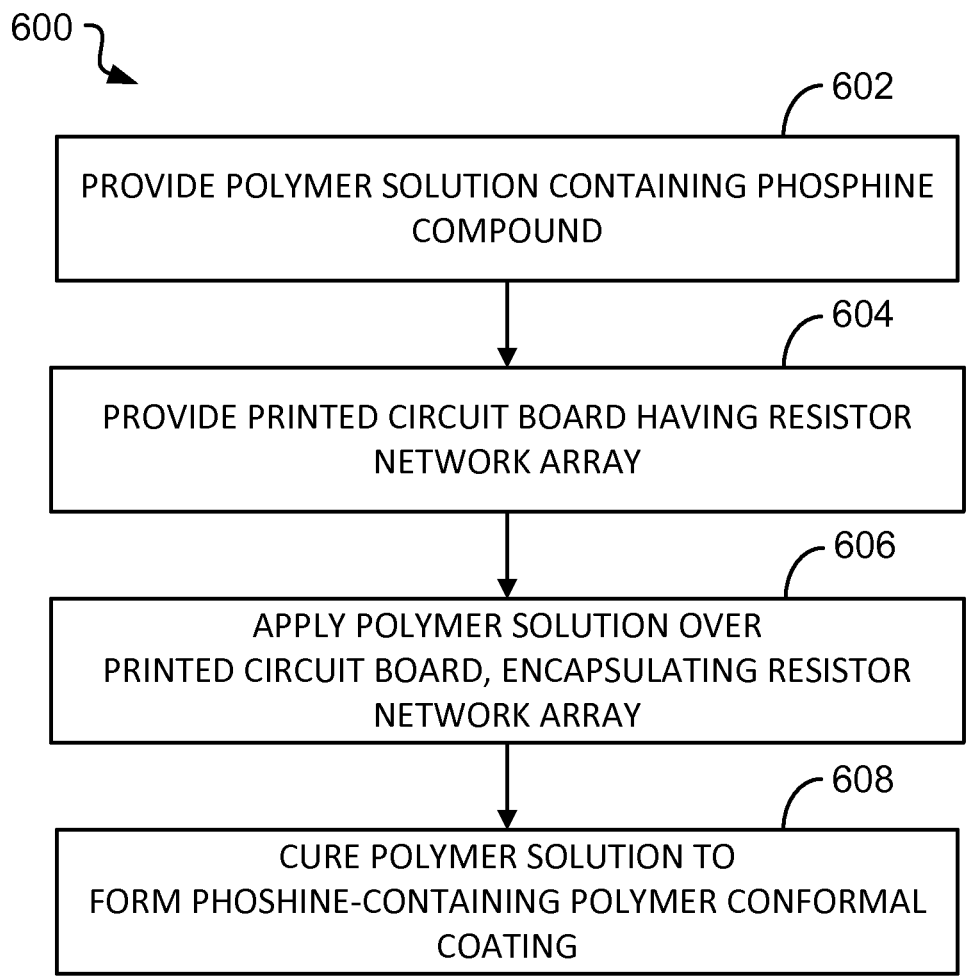
FIG. 6 is a flow chart diagram of a method for producing a resistor network array that utilizes a phosphine-containing polymer conformal coating to protect metal conductors according to the preferred embodiments of the present invention.

FIG. 6 is a flow chart diagram of a method 600 for producing a resistor network array that utilizes a phosphine-containing polymer conformal coating to protect metal conductors according to the preferred embodiments of the present invention. Method 600 sets forth the preferred order of steps. It must be understood, however, that the various steps may occur simultaneously or at other times relative to one another. Method 600 begins by providing a polymer solution containing a phosphine compound (step 602). The phosphine compound is impregnated into and/or covalently bonded to the polymer of the polymer solution. For example, the polymer solution may be prepared by reacting a substituted phenyl phosphine and a substituted siloxane in acidic solution in the presence of ethanol. An example for the preparation of a substituted phosphine polysiloxane conformal coating is set forth in Equation (1):

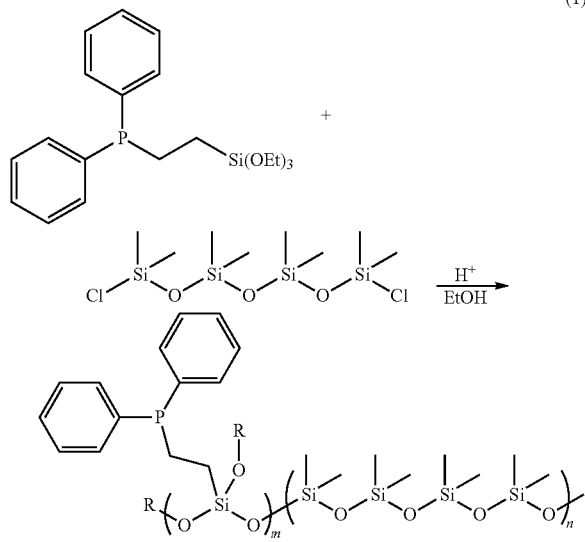

(1)

wherein each silicon atom in the substituted polysiloxane is attached to a hydrogen atom, an alkyl group, or an aryl group; and wherein:

R is a hydrogen atom, an alkyl group, or an aryl group,
m is an integer of at least 1, and
n is an integer of at least 1.

Method 600 continues by providing a resistor network array mounted on a printed circuit board (step 604). For example, the resistor network array may include gate resistors electrically connected by silver-bearing metal conductors (e.g., termination structures each having one or more silver-containing layers). The polymer solution is applied onto the printed circuit board to encapsulate the resistor network array (step 606). Preferably, the polymer solution is applied in an at least partially uncured state by dipping, spraying, spin-coating, casting, brushing, rolling, syringe, or any other suitable deposition process. Then, the polymer solution is cured to thereby produce the conformal coating (step 608). Generally, the process used to cure the polymer solution will vary based on the particular polymer solution used. For example, the polymer solution may be cured in a conventional drying process.

One skilled in the art will appreciate that many variations are possible within the scope of the present invention. For example, the preferred embodiments of the present invention are described above in the context of protecting metal conductors of electronic devices from corrosion caused by sulfur components in the air. One skilled in the art will appreciate, however, that the present invention can also apply to preventing corrosion to any metal surface, such as the metal surfaces of an automobile. Thus, while the present invention has been particularly shown and described with reference to the preferred embodiments thereof, it will be understood by those skilled in the art that these and other changes in form and detail may be made therein without departing from the spirit and scope of the present invention.

The apparatus and process described above limits a choice in material used in the conformal coating used. Described below is an apparatus and method that allows a wide choice in conformal coating materials usable to eliminate elemental sulfur penetration through the conformal coating.

The core idea to allow a wider range in conformal materials is to modify porous silica filler particles with a gettering functionality such as phosphines and other gettering functionalities known to those skilled in the art. The modified porous silica filler particles are then added to a conformal coating used to coat electrical components in an electrical system, such as chips, circuit modules, or circuit printed wiring boards. The gettering functionality binds to elemental sulfur (S8) and prevents the elemental sulfur from getting through the conformal coating where the elemental sulfur would cause corrosion in metallurgy on the electrical component. The porous silica filler particles provide an increased effective surface area upon which the gettering functionality may attach. Described earlier was a conformal coating 330 composed of a polymer into which a phosphines compound is impregnated and/or covalently bonded. Use of modified porous silica filler particles having phosphines or other sulfur getterers allows use of conformal coating materials not having polymers with which phosphine compounds will bond.

Examples of porous silica filler materials include MCM-41, SBA-15, or other porous silica filler particles. The modified porous silica filler particles would be prepared by silating an existing porous particle such as MCM-41, SBA-15, or other particles prepared through templating using surfactants or other means known to those skilled in the art. Additionally, the modified porous silica particles can be prepared via a copolymerization during the particle formation. Typically, modified porous silica filler particles are prepared through the sol-gel polymerization of a tetraalkoxysilane such as tetraethyorthosilicate (TEOS) or other surfactants known to those skilled in the art in the presence of a surfactant such as Cetyl trimethylammonium bromide (CTAB). To modify the porous silica filler particle surface in-situ during the polymerization, the TEOS may be copolymerized with 2-(Diphenylphosphino)ethyltriethoxysilane or other trialkoxysilane containing amine or phosphines functionalities.

A skeletal depiction of triphenylphosphine-sulfide phosphine compound is depicted below, showing sulfur combined with phosphines and thereby being removed from further incursion through the conformal coating to the metal conductors under the conformal coating. The chemical equation for this combination is:

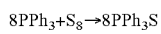
$8PPh_3 + S_8 \rightarrow 8PPh_3S$

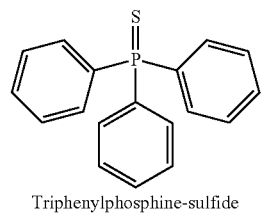 [SMILES: S=P(c1ccccc1)(c1ccccc1)c1ccccc1]
Triphenylphosphine-sulfide

It is known that triphenylphosphine will also combine with atmospheric oxygen, slowly, at elevated temperatures of approximately 140° C. (Centigrade); however at temperatures electronic equipment typically operates (room temperature to approximately 125° C., very little atmospheric oxygen will combine with the triphenylphosphine, providing long life gettering functionality of elemental sulfur by the triphenylphosphine.

A primary advantage of using porous silica filler particles modified with a gettering functionality such as phosphines and others known to those skilled in the art is that the gettering material is covalent bonded to the porous silica filler particles, therefore allowing greater freedom in selecting the conformal coating material. MCM-41 is known to have a large amount of surface area for its size/weight, approximately 1000 square meters per gram, offering a large number of silicon atoms available for bonding with the phosphine (e.g., triphenylphosphine) molecules.

Figure 7:
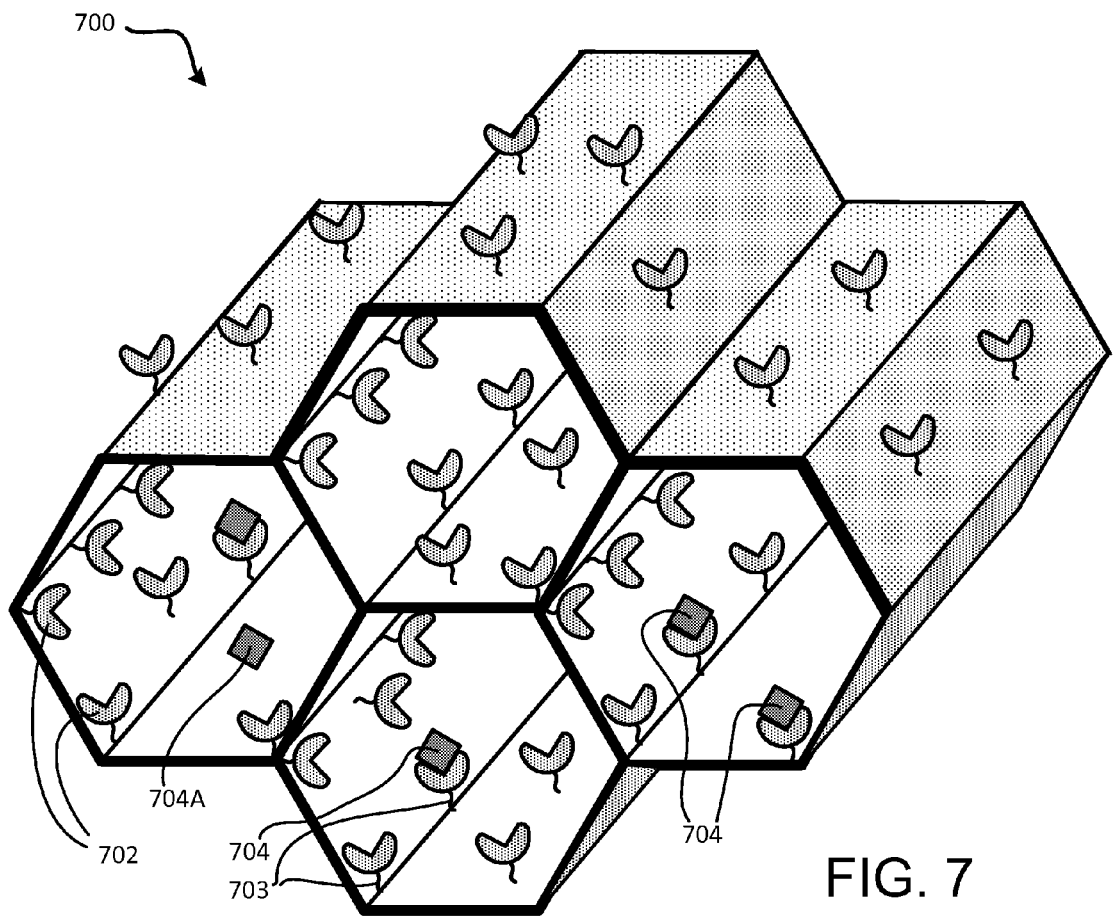
FIG. 7 shows a modified porous silica particle.

Turning now to FIG. 7, and using MCM-41 as an example porous silica filler particle, modified porous silica filler particle 700 is shown, comprising several "honeycomb" shaped MCM-41 hexagonal structures. For simplicity of drawing, phosphine (e.g., triphenylphosphine) molecules capable of gettering elemental sulfur are depicted as getters 702, attached by covalent bonds 703 to silicon atoms in modified porous silica filler particle 700. Elemental sulfur atoms 704 are shown captured by getters 702 in several places. Elemental sulfur atom 704A is shown having not yet been gettered by a getter 702.

Modified porous silica filler particles 700 may be prepared by silating an existing porous particle such as MCM-41, SBA-15 or other particles prepared through templating using surfactants or other means known to those skilled in the art. Additionally, as described above, the porous silica filler particles can be prepared via a copolymerization during the particle formation.

Figure 8:
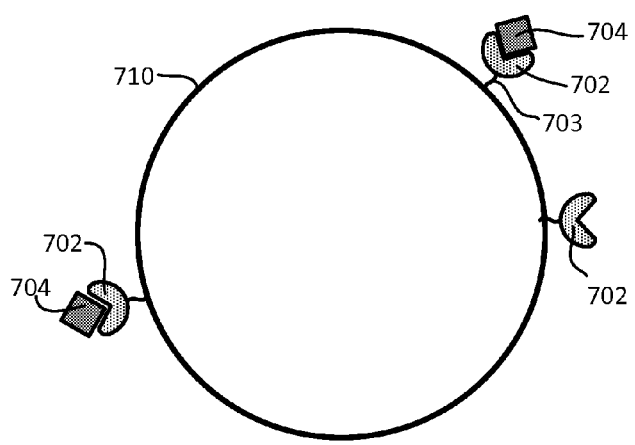
FIG. 8 shows a non-porous silica particle.

In contrast, FIG. 8 shows a solid particle 710 comprising silicon atoms. Again, phosphine molecules 702 may be attached to silicon atoms in solid particle 710 by covalent bonds 703 to getter elemental sulphur atoms 704, but since solid particle 710 does not have an inside also exposed, covalent bonds 703 may only occur at the relatively limited surface area of solid particle 710.

Figure 9:
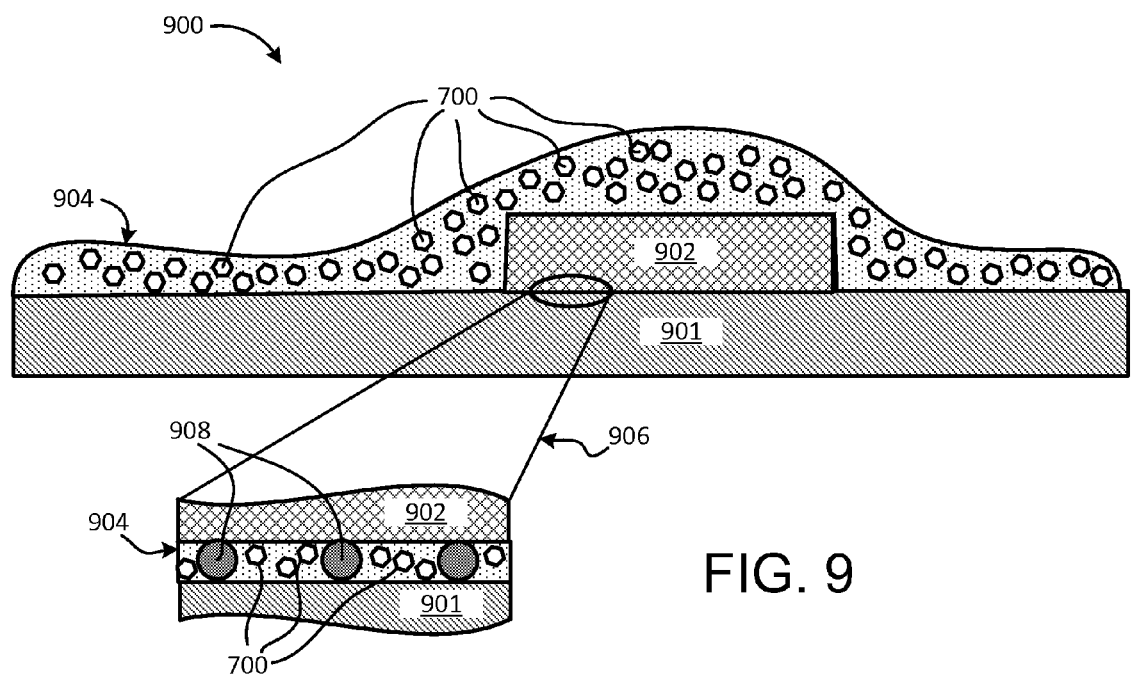
FIG. 9 shows an electronic package using a conformal coating comprising modified porous silica particles.

FIG. 9 shows electronic package 900 which comprises a substrate 901, which may be a printed wiring card, a ceramic module, an organic module, a silicon carrier, or other electronic packaging element. Electronic component 902 is mechanically and electrically attached to substrate 901. Electronic component 902 may be a semiconductor chip, a ceramic module, an organic module, or other electronic packaging element. Conformal coating 904 may cover at least a portion of substrate 901. Conformal coating 904 may cover at least a portion of electronic component 902. As shown as an example, conformal coating 904 covers both a top surface of substrate 901 and electronic component 902. A blown-up view 906 of an interconnection between substrate 901 and electronic component 902 is shown, illustrating a "solder bump connection" (such as a C4 connection) between substrate 901 and electronic component 902. Conformal coating 904 may fill the space between substrate 901 and electronic component 902 and surround the solder bumps 908, thereby also protecting solder bumps 908 from elemental sulfur. Conformal coating 904 comprises a number of modified porous silica filler particles 700, the modified porous silica filler particles 700 gettering elemental sulfur atoms 704 (FIG. 7) before the elemental sulfur atoms can penetrate conformal coating 904 and cause corrosion in metal conductors on substrate 901 and/or electronic, component 902.

It will be understood that conformal coating 904 may be selectively applied to portions of electronic package 900. For example, a particular electronic component such as resistor 300 shown in FIGS. 3 and 4 may have conformal coating 904 applied over the particular component.

What is claimed is:

1. An apparatus, comprising:
a substrate;
an electronic component mounted on the substrate;
metal electrical conductors; and
a conformal coating covering the metal electrical conductors, wherein the conformal coating comprises a plurality of modified porous silica filler particles having a surface area of approximately 1000 square meters/gram with a gettering functionality covalently bonded to silicon atoms in the porous silica filler particles.

2. The apparatus as recited in claim 1, wherein the conformal coating is exposed to, and protects the metal electrical conductors from, a gaseous environment that includes elemental sulfur.

3. The apparatus of claim 1, wherein the metal electrical conductors comprise silver.

4. The apparatus of claim 1, the metal electrical connectors being on the substrate.

5. The apparatus of claim 1, the metal electrical conductors being on the electronic component.

6. The apparatus of claim 1, the metal electrical conductors used to electrically connect the substrate and the electronic component.

7. The apparatus of claim 1, the gettering functionality comprising a phosphine compound.

8. The apparatus as recited in claim 7, wherein the phosphine compound is selected from a group consisting of alkyl phosphines and aryl phosphines; and combinations thereof.

9. The apparatus as recited in claim 7, wherein the phosphine compound is selected from a group consisting of substituted or unsubstituted butyl phosphines and substituted or unsubstituted phenyl phosphines; and combinations thereof.

10. The apparatus as recited in claim 1, wherein the modified porous silica filler particles comprise Mobile Crystalline Material (MCM-41).

11. The apparatus as recited in claim 1, wherein the modified porous silica filler particles comprise SBA-15.

12. A conformal coating composition for protecting a metal surface from corrosion from sulfur-bearing gas, the conformal coating composition comprising:
modified porous silica filler particles having a surface area of approximately 1000 square meters/gram comprising a gettering function covalently bonded to silicon atoms in porous silica filler particles.

13. The conformal coating composition as recited in claim 12, wherein the gettering function is a phosphine compound.

14. The conformal coating composition as recited in claim 13, wherein the phosphine compound is selected from a group consisting of alkyl phosphines and aryl phosphines; and combinations thereof.

15. The conformal coating composition as recited in claim 13, wherein the phosphine compound is selected from a group consisting of substituted or unsubstituted tributyl phosphine and substituted or unsubstituted triphenyl phosphines; and combinations thereof.

16. The conformal coating composition as recited in claim 12, wherein the modified porous silica filler particles comprise MCM-41 (Mobile Crystalline Material).

17. The conformal coating composition as recited in claim 12, wherein the modified porous silica filler particles comprise SBA-15.

* * * * *